(12) United States Patent
Arknæs-Pedersen

(10) Patent No.: US 7,003,121 B1
(45) Date of Patent: Feb. 21, 2006

(54) METHOD AND AN APPARATUS FOR PROCESSING AN AUSCULTATION SIGNAL

(75) Inventor: Lars Arknæs-Pedersen, Struer (DK)

(73) Assignee: Bang & Olufsen Technology A/S, Struer (DK)

( * ) Notice: Subject to any disclaimer, the term of this patent is extended or adjusted under 35 U.S.C. 154(b) by 0 days.

(21) Appl. No.: 09/283,585

(22) Filed: Apr. 1, 1999

(30) Foreign Application Priority Data

Apr. 8, 1998 (DK) ...................................... 0515/98

(51) Int. Cl.
*A61B 7/04* (2006.01)

(52) U.S. Cl. ........................................ 381/67; 600/528
(58) Field of Classification Search ................. 381/67; 600/528, 586
See application file for complete search history.

(56) References Cited

U.S. PATENT DOCUMENTS

| 4,424,815 A | 1/1984 | Kuntz |
| 4,528,689 A | 7/1985 | Katz |
| 4,783,807 A | 11/1988 | Marley |
| 5,003,603 A | 3/1991 | Searcy et al. |
| 5,157,727 A | 10/1992 | Schloss |
| 5,971,936 A * | 10/1999 | Don Michael et al. ..... 600/528 |

FOREIGN PATENT DOCUMENTS

EP       0 723 258 A1    7/1996

* cited by examiner

*Primary Examiner*—Ping Lee
(74) *Attorney, Agent, or Firm*—David S. Safran

(57) ABSTRACT

A method of processing a signal representing an input sound signal is disclosed. The signal is divided in time into a plurality of signal segments, each having an individual duration of time. The signal segments are processed into an output signal of successive signal segments in such a way that at least one, preferably all, of the signal segments are repeated immediately and successively at least once in the output signal. Each signal segment is established in such a way that the duration of time of a majority, preferably all, of the signal segments is less than 60 ms. Thus, a sound signal can be reduced in speed by doubling the number of short cycles.

26 Claims, 8 Drawing Sheets

METHOD AND AN APPARATUS FOR PROCESSING AN AUSCULTATION SIGNAL

BACKGROUND OF THE INVENTION

1. Field of the Invention

The present invention relates to a method of processing a signal representing an input sound signal, the signal being divided in time into a plurality of signal segments, each having an individual duration of time, the signal segments being processed into an output signal of successive signal segments, the signal segments being processed in such a way that at least one, preferably all signal segments are repeated at least once in said output signal.

Moreover, the present invention relates an apparatus, and in particular to an electronic stethoscope for use in cardiology.

2. Description of Relation Art

Through the recent years physicians have been provided with an impressive arsenal of instrumentation for the diagnosis of cardiovascular diseases. Such an instrument is the well known stethoscope used to detect sounds originating from the heart and adjacent large vessels. Sound monitoring of the heart, or auscultation in general, is an important aspect in the evaluation of the physical condition of an individual, and is particularly important in the diagnosis of certain pathological conditions which manifest themselves by abnormal sounds.

When using a normal bifurcated stethoscope with binaural earpieces and a bell or diaphragm for receiving the sound signal, it is difficult to distinguish the sound elements in fast beating hearts, e.g. infants, but also when auscultating patients with a 'normal' heart rate, it can be difficult to observe split heart sounds or a weak murmur located near a primary heart sound.

Today it is possible to process the information residing in the auscultation signal electronically by using knowledge obtained by clinical research. Electronic stethoscopes make it possible to modify the physiological signal, but the approaches are mostly based on changes of the frequency components in the signal, which makes it difficult for a physician, trained in the use of the conventional stethoscopes, to recognize the signal.

This leads to the goal of creating a stethoscope or an apparatus for auscultation in general that makes it easier for the pathologist to distinguish between the different sound elements in even fast heart sounds. Since the pathologists partly base their diagnosis on the heart sounds, it is of great importance that an exact reproduction of the sound elements in the sound signal is performed, meaning that there should be no change in the pitch of the signal and no dissonance should be added as a result of the reproduction algorithm. If either distortion or change of pitch is present, it could lead to a wrong interpretation of the heart sounds, resulting in incorrect diagnoses by the physicians.

U.S. Pat. No. 4,528,689 discloses the idea of a method for artificially slowing down an analyzed sound signal. It is done by first low-pass filtering the sound signal from the heart and then splitting the signal, which varies cyclically from zero crossing to zero crossing, into a number of cycles, and each cycle is repeated successively. These repetitions of half-periods of a sound representing signal result in a slow version of the original sound having the original pitch.

SUMMARY OF THE INVENTION

Consequently, the prior art involves the problem that the resulting signal provides echoes in such a way that a listener may obtain confused results while listening to the generated slow signal. Appearances of echoes might result in a wrong interpretation of some sound elements, and these sound elements are often of vital importance. When identifying a heart disease, this method might lead to incorrect diagnoses. Further the method introduces click sounds at the points where successive cycles are pasted together. Dissonance as click sounds might also lead to disturbance of the auscultation signal and even wrong diagnoses. Moreover, the prior art does not take into account that the auscultation signal can be acquired under disturbed or varying conditions. Apparently, the method has found very little commercial use, if any.

It is an object of the invention to provide a method which will be able to slow down sound signals especially sound signals representing auscultation signals like heart sounds, while still obtaining the original pitch with a minimum of echo in the resulting slowed down signal. This is achieved, when the method mentioned in the opening paragraph is characterized in that each signal segment is established such that the duration of time of substantially all the signal segments is less than a limit of 50 ms.

Consequently, it is possible for a listener to distinguish between the different sounds of the generated output signal, as the audio signals generated according to the invention are ideally free of any perception of echo or significant distortion. This possibility of eliminating the echo perception for a listener makes the invention a unique and essential part of any analysis tool for supporting signal analyzing based on subjective recorded and processed audio signals. Using this invention, the physician will not be able to distinguish between a 'real' auscultation signal and a processed auscultation signal, as the processed signal will be perceived as a 'real' signal.

This feature is of particular importance when speaking about sound signals, which can only be analyzed by means of a subjective analysis performed by a listener. Fields in which the invention will provide important support include evaluation of sound signals emitted from the heart beats. A trained listener, such as a pathologist, will thus have the possibility of getting a full expression of the actual emitted sound, even if the emitted signal is a high-speed signal, such as the one provided by the heart of a child.

In an expedient embodiment the auscultation signal is filtered iteratively by means of an iterative filtering process until the duration of time of substantially all the signal segments is less than the limit. Thereby, the signal processing is capable of adapting itself to a broad spectrum of different auscultation signals.

This is possible in particular when the iterative filtering process is terminated when the filtered signal does not consist of signal segments having a duration of time which is longer than the limit. Thereby, an auscultation signal consisting of relatively small signal amplitudes at low frequencies is not filtered too much, which otherwise would cause an excessive number of segments having a short duration of time. An excessive number of segments having a short duration of time will increase the computational effort required for repeating the segments.

When the limit is less than 40 ms, preferably 30 ms a very preferred embodiment according to the invention is achieved, as pilot tests have turned out to be very successful with respect to e.g. stethoscopes. The embodiment of the invention thus provides no perception of echo even if the signal consists of signal components in a frequency spectrum of a recorded heart sound signal of between approximately 20 Hz–2 kHz.

In an expedient embodiment the auscultation signal is pre-filtered iteratively by means of a high-pass filter until the duration of time of signal segments is less than the limit. Thereby, a tangible stopping criterion for the iterative filtering process is provided.

When, moreover, the output signal is post-filtered iteratively with a filter having an amplitude transfer function corresponding to the inverse amplitude transfer function of the high-pass filter, the frequency-amplitude response of the pre- and post-filtering process is substantially flat.

In an expedient embodiment the iterative filtering process is terminated when the auscultation signal has been filtered a specified number of times and that an indicator signal indicating termination of the filtering process is provided. Thereby it is possible to select a threshold for a maximum number of allowable filtering iterations when reached may generate a warning signal.

Since successive repeating of signal segments having a relatively short duration will result in a poor sound quality at relatively high frequencies the signal segments having a relatively short duration of time are patched together to form a coherent segment consisting of at least three zero-crossings, which coherent segment is repeated at least once.

When the input signal is divided into signal segments at zero crossings, excessive high-frequency components are avoided which otherwise can ruin the sound quality.

When the input signal is divided into signal segments such that the gradients of neighboring signal segments of the output signal are substantially equal, and wherein the neighboring signal segments are level-compensated, high-frequency components are reduced to a minimum.

In an expedient embodiment the signal divided segments are multiplied or filtered by means of a window function such that the transitions between neighbouring signal segments are smoothed.

In a simple and preferred embodiment of the invention, the signal segments are reversed with respect to time before the repetition, thus ensuring that the repetitions will have a kind of short duration "backward" masking. It should be noted that the necessary signal processing for obtaining the inverse repetition described above is minimal.

Moreover, the signal segments in the output signal can be mirrored about a time axis in order to further smooth the transitions between neighbouring segments.

In a preferred embodiment the auscultation signal is pre-filtered by a high-pass filter such that further zero crossings may be obtained.

Moreover, the invention relates to an apparatus and in particular to a stethoscope.

BRIEF DESCRIPTION OF THE DRAWINGS

The invention will be explained more fully below in connection with a preferred embodiment and with reference to the drawing, in which.

DETAILED DESCRIPTION OF PREFERRED EMBODIMENTS

Figure 1:
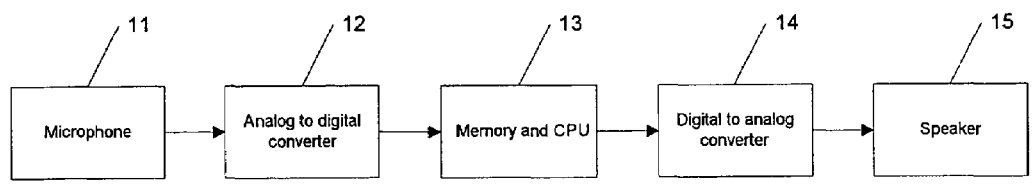
FIG. 1 illustrates the basic parts of an electronic stethoscope.

FIG. 1 illustrates an electronic stethoscope consisting of a microphone 11 connected to an analog to digital converter 12 from which the output is connected to a memory and central processing unit 13. The memory and central processing unit 13 is connected to a digital to analog converter 14 and the output is connected to a speaker 15. Thereby an auscultation signal is acquired, processed, and reproduced as a sound signal.

In use, the physician places the microphone 11, which may be in the shape of a bell, on the patient's chest and the sound is recorded and processed in the processing unit 13. It is possible to hear the processed signal by using the speaker or speakers 15 connected to the digital to analog converter 14.

Figure 2:
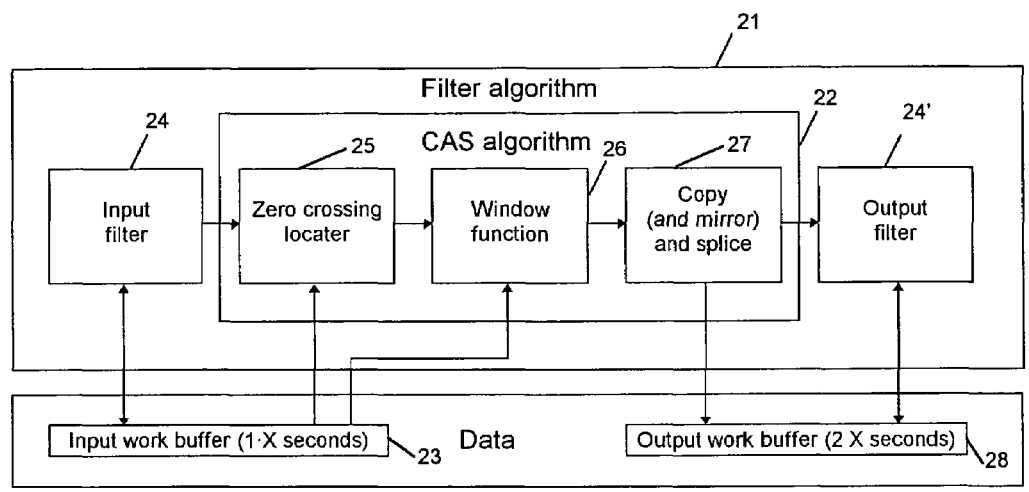
FIG. 2 shows the half rate algorithm consisting of a filter algorithm, a copy-and-splice (CAS) algorithm and the buffers.

FIG. 2 illustrates the half rate algorithm performed by the central processing unit and memory 13. This algorithm consists of two parts—a filter algorithm 21 and a copy-and-splice (CAS) algorithm 22. The recorded data is placed in the input work buffer 23, and then filtered using an iterative filter 24 and 24'. The CAS algorithm 22 is performed between the filters 24 and 24'. The CAS algorithm consists of a zero crossing locator 25, a window function 26 and a copy and splice function 27. The algorithm halves the rate of the sound, resulting in a doubling of the length of the sound signal, whereby the signal has twice the original duration in the output work buffer 28.

Figure 3A:
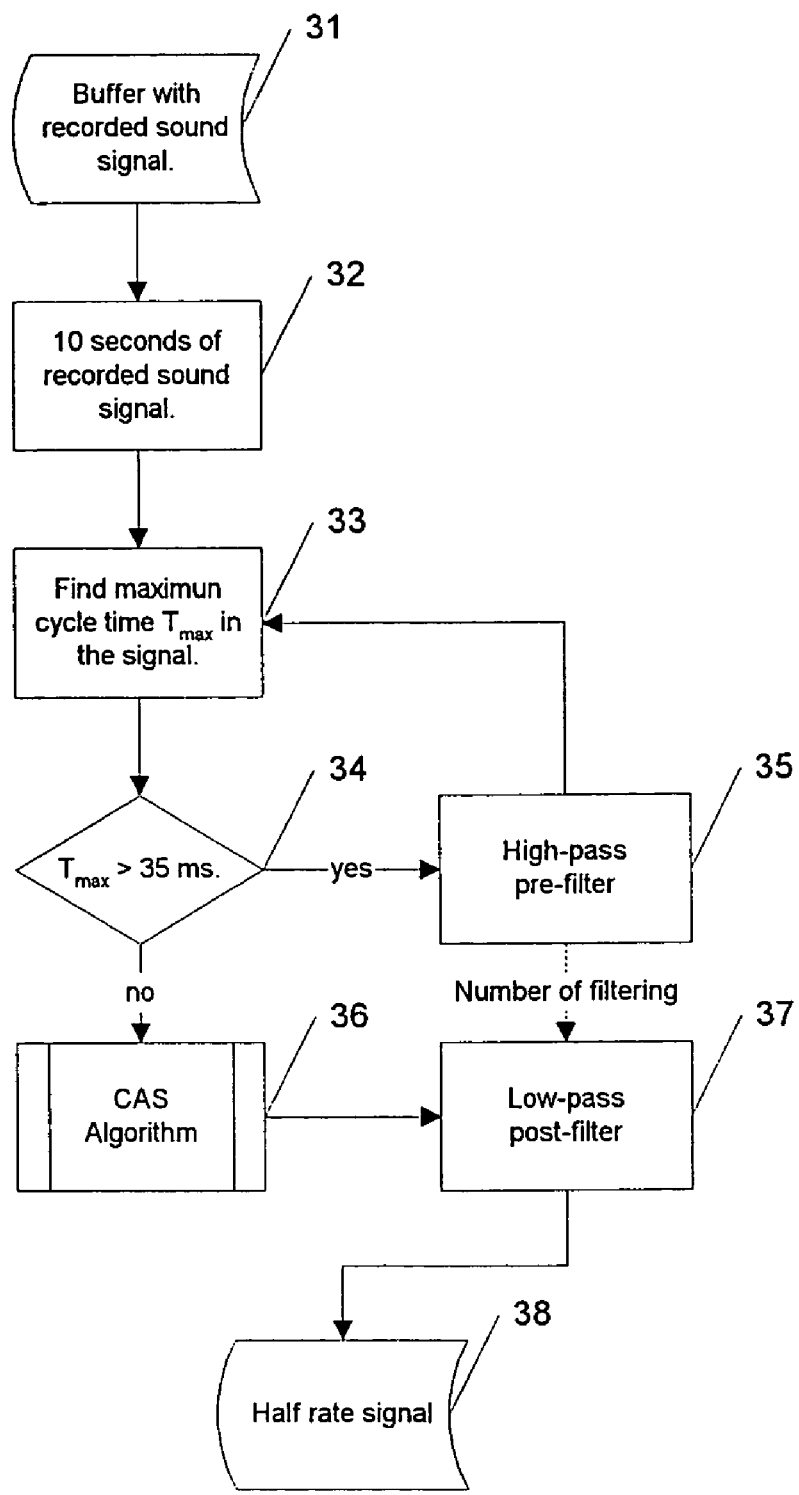
FIG. 3a shows the iterative filter process of the filter algorithm and FIGS. 3b, 3c, 3d and 3e illustrates the algorithm performed stepwise on a heart signal.

The iterative filter algorithm including the pre-filter 35 and the post-filter 37 is shown in FIG. 3a. The input signal is pre-filtered. This is done in order to amplify the high frequency signal elements and attenuate the lower frequencies. In order to reduce the processor power needed by the algorithm, the algorithm is performed on the sound signal part by part. In a preferred embodiment it is run on parts with a 10 second duration. First, the time period 32 is singled out of the recorded sound signal 31, secondly an algorithm 33 determines the maximum cycle time. In 34 the algorithm checks whether the cycle time is above a predetermined value $T_{max}$. If it is above the predetermined value, the signal part is filtered using a high-pass filter 35, and this step is repeated until the cycle time is below the predetermined value. Then, the CAS algorithm is executed in 36, in the described embodiment the algorithm doubles the length of the sound signal. Finally, the signal part is post-filtered the same number of times as it was pre-filtered using a low pass filter 37 which has an inverse transfer function with respect to the pre-filter 35. The post-filtering 37 amplifies the low frequencies (long cycles) in the same way as they were attenuated in the pre-filter 35 in order to ensure a flat frequency response from input to output. To avoid echo, the value $T_{max}$ should be chosen according to the time constant of the ear, which is the response time for the human ear after hearing a first sound.

Figure 3B:
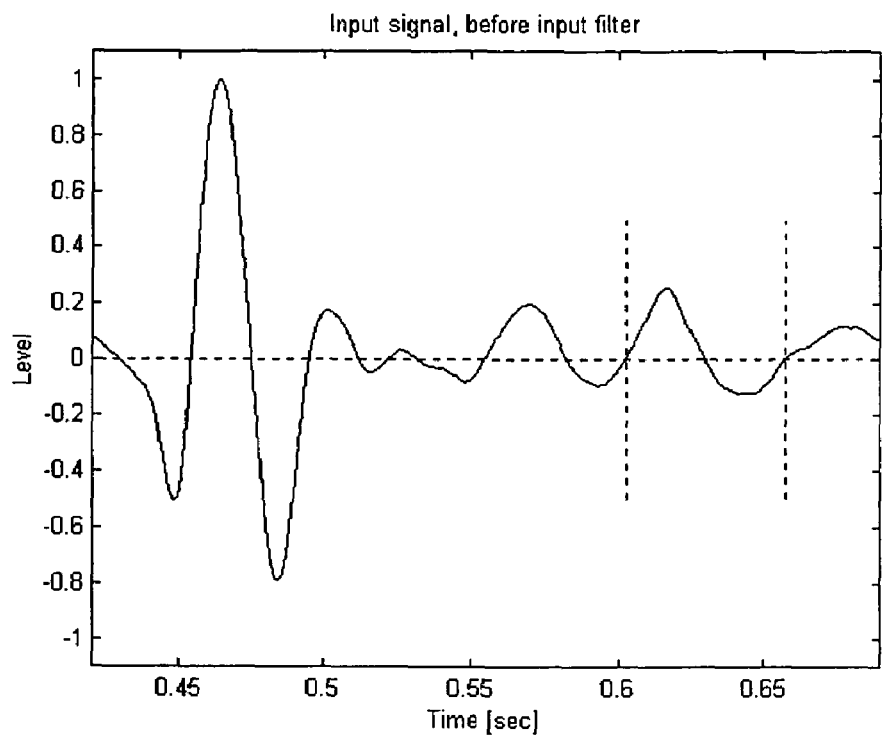
Figure 3C:
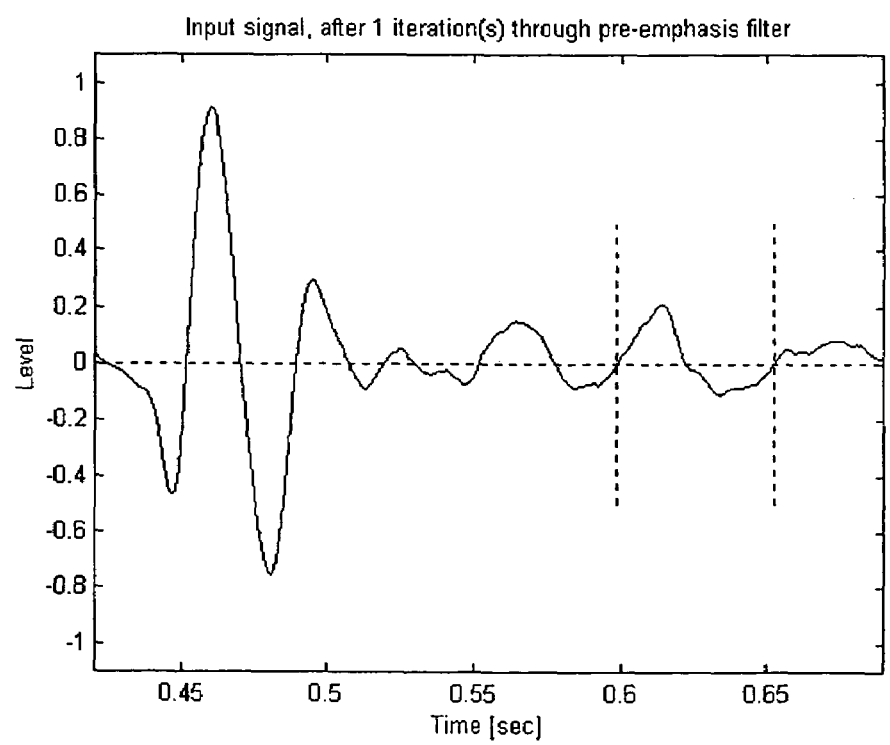
Figure 3D:
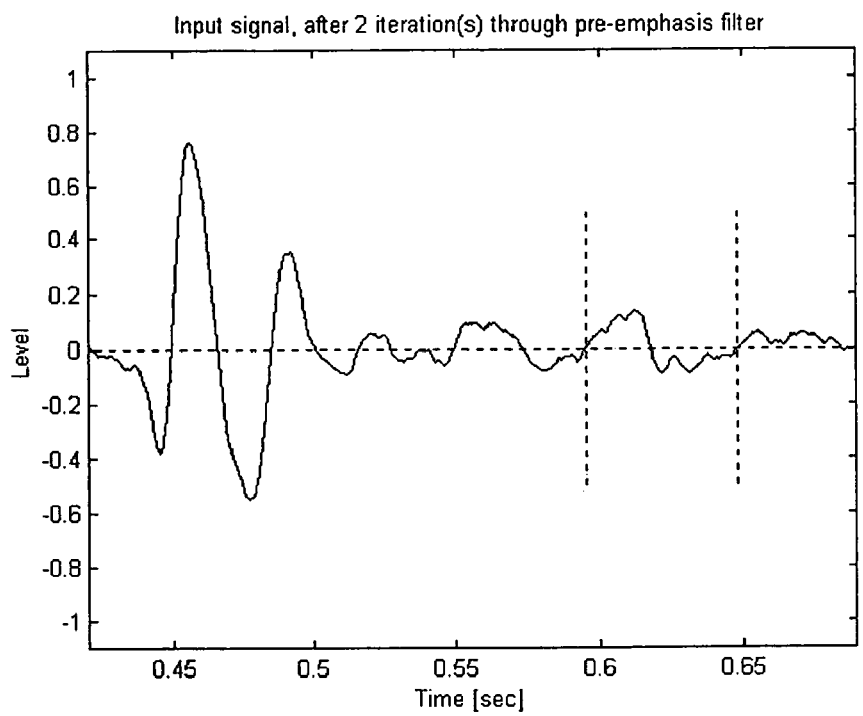
Figure 3E:
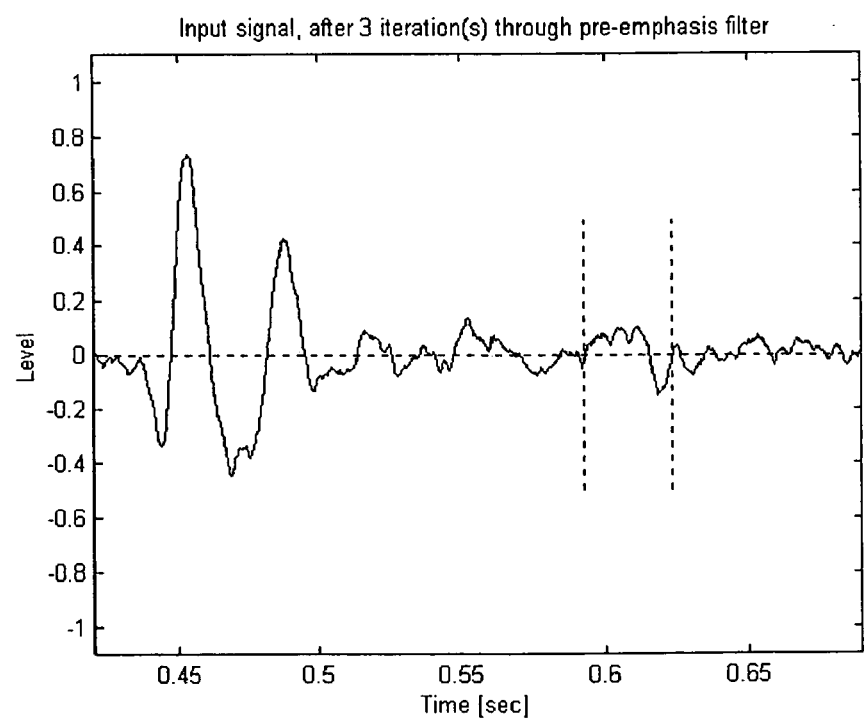

To illustrate the effect of the iterative filter, a signal is shown before filtering in FIG. 3b. Then the signal is shown after one filtering in FIG. 3c, followed by the signal after filtering twice. Finally, the signal is shown after being filtered three times resulting in an extra zero crossing in the time interval between 0,6s and 0.65s.

Figure 4:
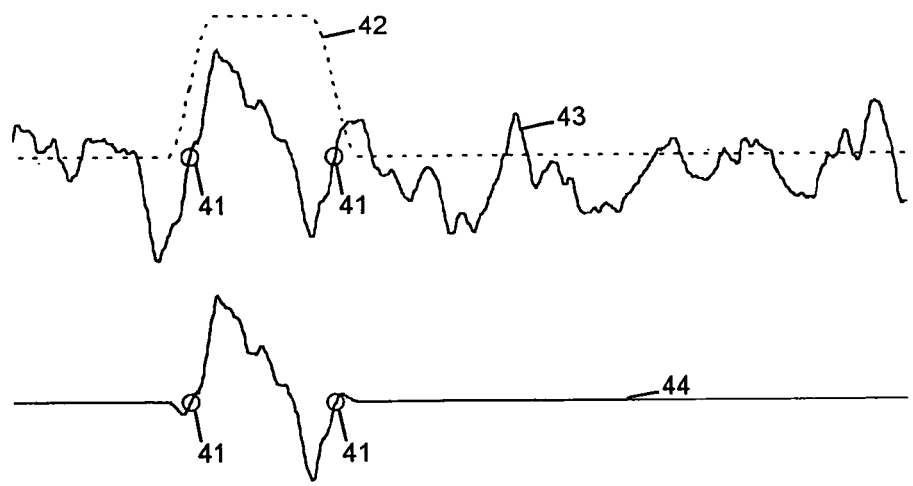
FIG. 4 illustrates a signal with zero crossings and a window function.

The CAS algorithm shown in FIG. 2 will be described in detail below. A sample signal 43 is shown in FIG. 4. The zero crossing locator 25 in FIG. 2 locates the negative to positive transitions 41 (zero crossings) in the filtered input signal. This means that the boundaries of all cycles in the signal are located. These locations will be used by the window function 26 shown in FIG. 2. The window function 26 is used to prevent click sounds from occurring when succeeding cycles are patched together, the start and end portion of each cycle are smoothed (faded in/out). The window 42 will generate signal portions that are a bit longer than those of the cycle itself (zero crossing to zero crossing), this is done to enable smooth overlapping sections, from one cycle to the next. In the preferred embodiment the amplitude (weight) of the window 42 at its centre equals 1.0, and the weight at the zero crossings 41 equals 0.5. This results in the cycle after cutting 44 being a bit longer than from zero crossing to zero crossing, providing smooth transitions between succeeding cycles.

Figure 5:
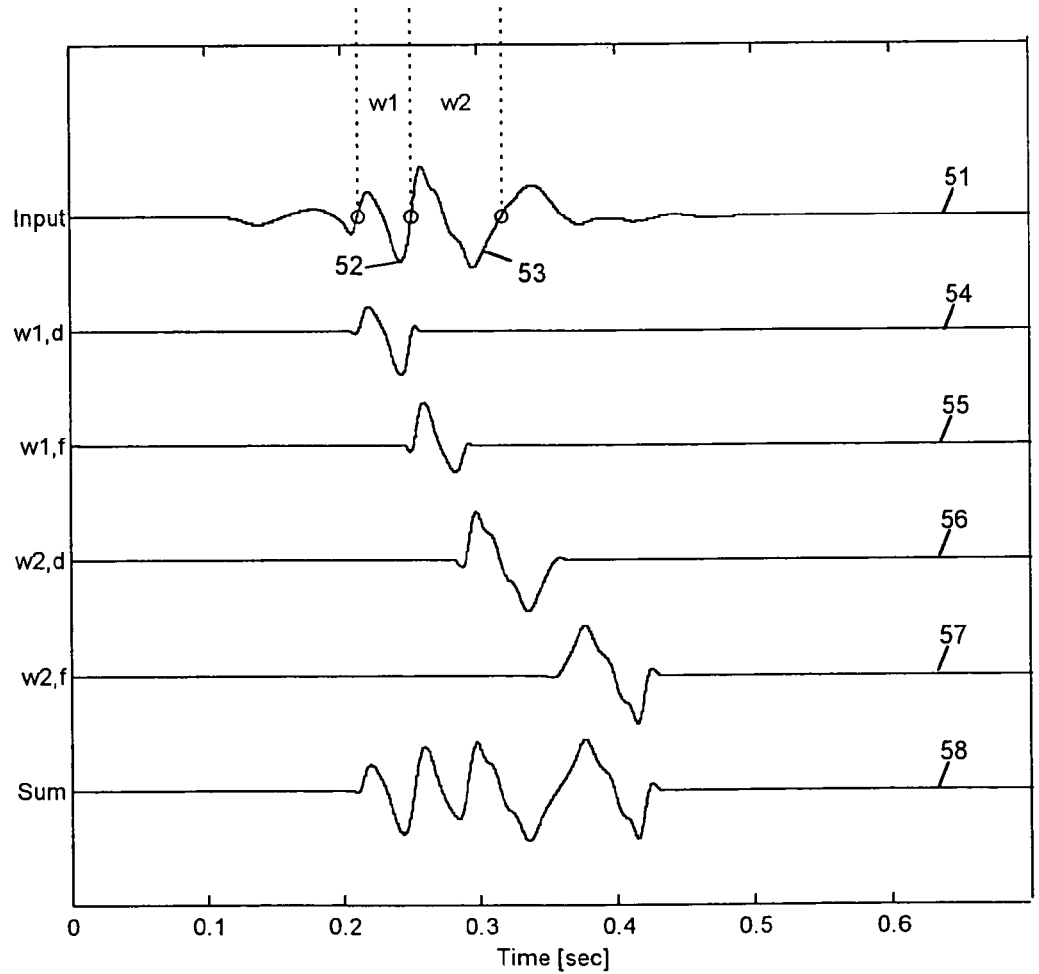
FIG. 5 illustrates the CAS algorithm when performed on a sample signal of two cycles.

An example of how the output signal of a half-rate signal is made by using the copy and splice process 27 from FIG. 2 is shown in FIG. 5. A sample input signal after pre-filtering 51 consists of two cycles 52 and 53. The cycle 52 is cut from the sample signal 51, using the window 42 shown in FIG. 4, providing the signal 54. It is seen that the window described above used on the cycle 52 results in signal 54 with longer duration than the identified cycle 52. The signal 54 is then copied and shifted in time resulting in the signal 55, which succeeds the signal 54 with overlapping zero crossing. In a preferred embodiment as shown in FIG. 5, the copy 55 is mirrored in both the horizontal axis and the vertical i.e. reversed in time and mirrored about a time axis. Tests have shown that this results in a minimum chance of echo perception. The similar is done to the cycle 53, first the cycle is cut from the signal 51 using the window 42 providing the signal 56. Then the signal 56 is copied and mirrored providing the signal 57. The signals 54, 55, 56 and 57 are added causing a reduction of the rate of the signal 51 by 50%. The original pitch is obtained, and performing this process on only fast cycles, the listener will not experience any echoes.

This method used on a heart signal is shown in the following.

Figure 6:
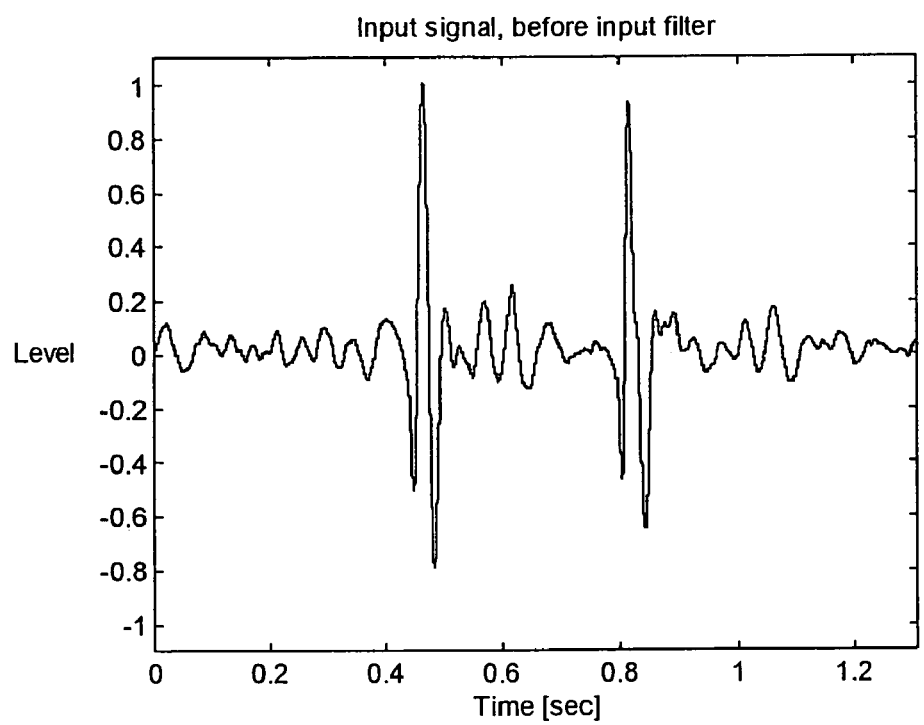
FIG. 6 illustrates a heart signal before pre-filtering.

FIG. 6 shows a heart signal before filtering with the iterative high-pass pre-filter 24 from FIG. 2. It is obvious that the signal includes some slow cycles.

Figure 7:
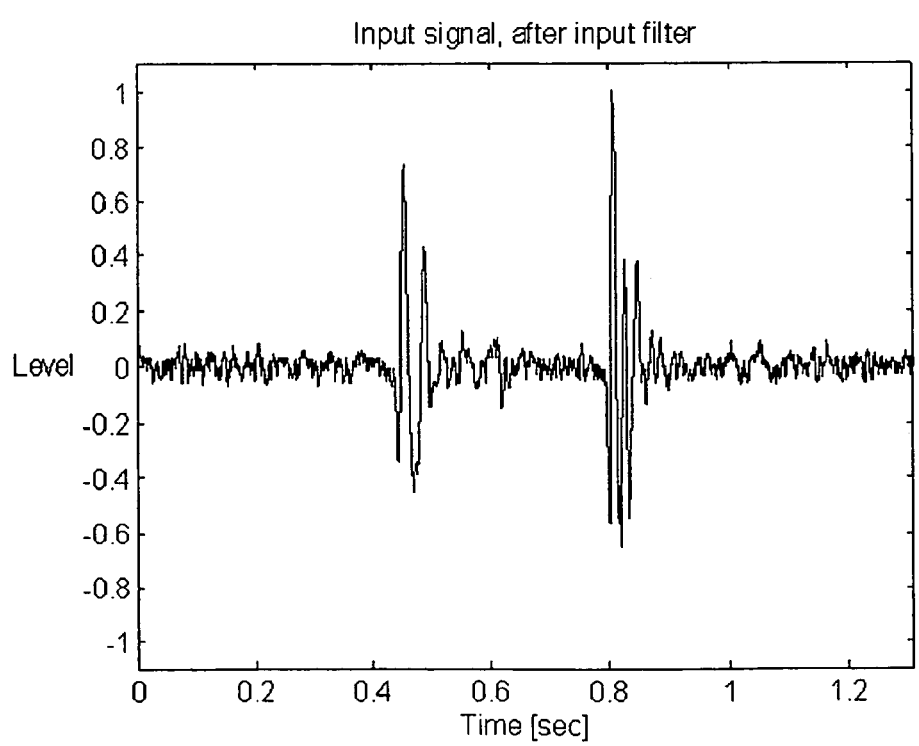
FIG. 7 illustrates a heart signal after pre-filtering.

FIG. 7 shows the signal after filtering with the high pass filter 24, and it is obvious that the slow cycles have been attenuated resulting in only fast cycles.

Figure 8:
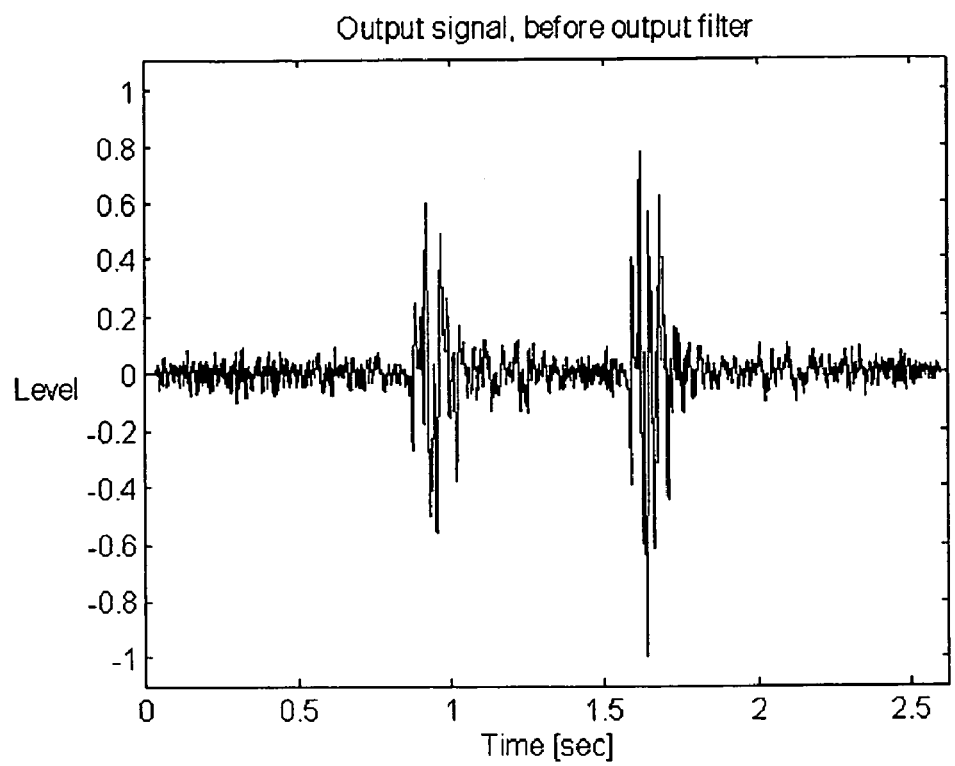
FIG. 8 illustrates a half rate heart signal before post-filtering.

FIG. 8 shows the pre-filtered heart signal as it is before post-filtering. The length of the signal has been doubled using the CAS algorithm.

Figure 9:
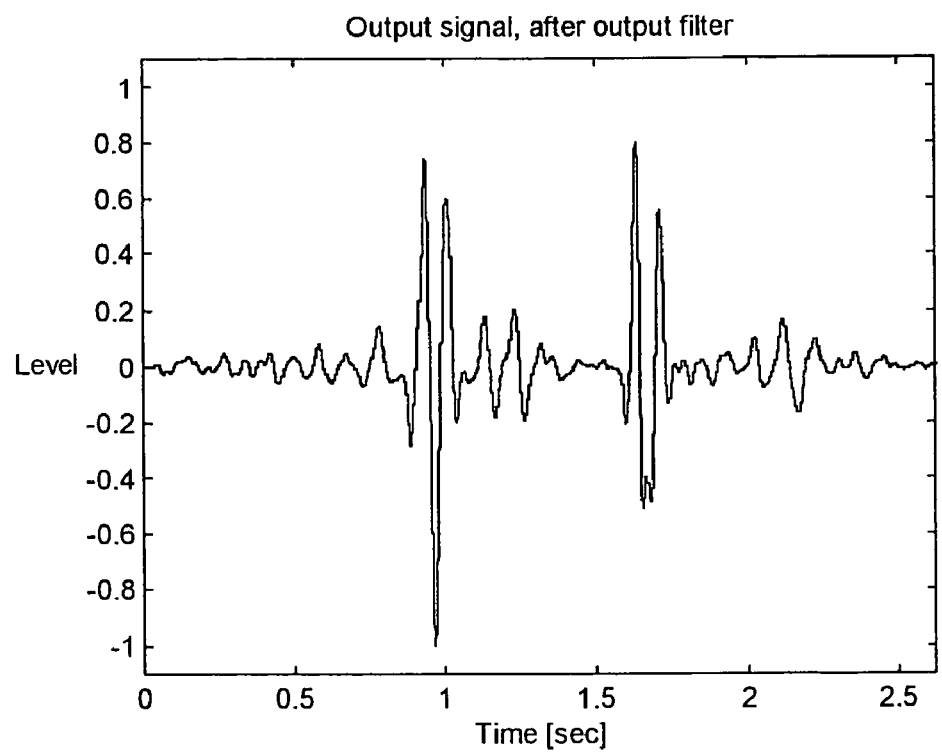
FIG. 9 illustrates a half rate heart signal after post-filtering.

FIG. 9 shows the output signal after post-filtering. The signal has been post-filtered the same number of times as it was pre-filtered. The rate of the original sound signal has now been halved and the physician listening to this halved version will not be able to perceive any echo.

Figure 10A:
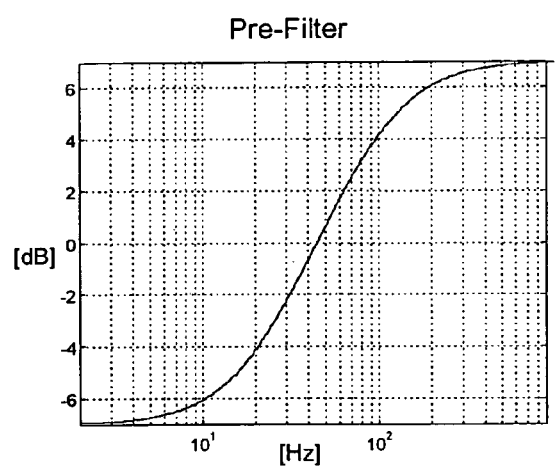
FIG. 10a illustrates the transfer function of pre-filter and FIG. 10b illustrates the post-filter.
Figure 10B:
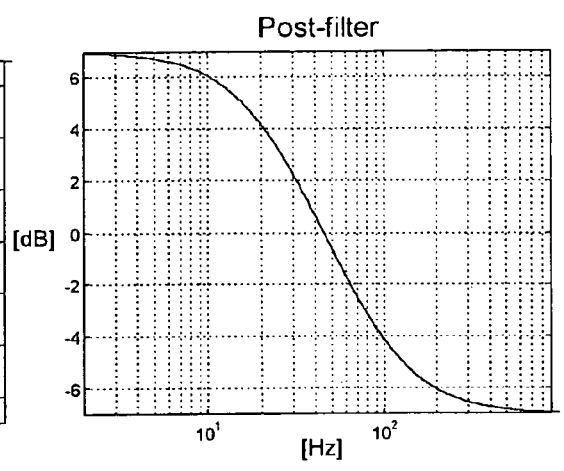

FIGS. 10a–10b shows the pre-filter and the post-filter, which in combination have a flat frequency response.

It should be noted that in this preferred embodiment of the invention the rate of the signal has been halved but it is also possible to reduce the speed by another fraction. This reduction depends on how many times the cycles are repeated. In this embodiment cycles were used as the segments to be copied, but other methods could also be used to define a segment. Though it is advantageously to use segments that makes it possible to get a smooth transition between neighboring segments.

Further, it should be noted that the number of iterations in the iterative filter depends on the auscultation signal in question. Typically, an auscultation signal acquired from the rib-cage of an adult breathing normally requires 2–3 iterations, whereas an auscultation signal acquired from the lungs of an adult breathing normally requires 1–2 iterations. A maximum number of iterations is specified to 5 iterations.

Still further, it should be noted that iterative filter can use another stopping criteria e.g. Tmax<25 ms and/or that a specified maximum number of iterations has been reached. When a maximum number of iterations has been reached a signal can be provided which can be used to warn a user and/or terminate processing of an actual auscultation signal. The stopping criteria depends on the iterative filter itself and any filtering of the auscultation signal prior to the iterative filtering.

Experiments has shown that when a signal input to the CAS algorithm comprises many segments having a short duration of time the sound quality of the reproduced sound signal is ruined. Therefore, the iterative filter having a stopping criteria ensures that there is not generated an excessive number of segments having a short duration of time.

However the CAS algorithm can be adapted to handle a succession of segments having a short duration of time (e.g. less than 4–5 ms) if such a succession occurs.

When a succession of segments having a short duration of time is detected, the CAS algorithm patches the succession of segments together to form a coherent segment, which coherent segment is repeated a specified number of times corresponding to the rate at which the auscultation signal shall be slowed down. It should be noted that the coherent segment corresponds to a given part of the auscultation signal wherein there is a number of zero-crossings.

Another way to obtain additional zero-crossings in the auscultation signal would be to process the signal through a linear prediction-error filter. In this case, the function of the prediction-error filter would be to whiten the signal, so further zero-crossings would occur. The coefficients used in the all-zero linear prediction-error filter can be found, using well known analysis methods like "Levinson-Durbin recursion", "Burg algorithm" or others. The same coefficients are used in a all-pole output synthesizer filter, to which the output signal from the CAS algorithm is applied. The output synthesizer filter is used to ensure a flat frequency response from input to output.

The invention can be embodied as a part of a stethoscope or any other instrument or apparatus. The physical embodiment of a stethoscope according to the invention can be embodied e.g. as shown in FIG. 1 of U.S. Pat. No. 4,528,689. Additionally, a stethoscope according to the invention may comprise a readout of a heart rate calculated from the auscultation signal.

In a preferred embodiment segments are defined as a part of a signal from a zero-crossing having a positive or negative gradient to a zero-crossing having a positive or negative gradient, respectively.

Alternatively, the invention may be embodied as a computer program or a part of a computer program, which may be loaded into the memory of a computer and executed therefrom. The computer program may be distributed by means of any data storage or data transmission medium. The storage media can be magnetic tape, optical disc, compact disc (CD or CD-ROM), mini-disc, hard disk, floppy disk, ferroelectric memory, electrically erasable programmable read only memory (EEPROM), flash memory, EPROM, read only memory (ROM), static random access memory (SRAM), dynamic random access memory (DRAM), ferromagnetic memory, optical storage, charge coupled devices, smart cards, etc. The transmission medium can be a network, e.g. a local area network (LAN), a wide area network (WAN), or any combination thereof, e.g. the Internet. The network may comprise wire and wire-less communication links. Via the network a software embodiment (i.e. a program) of the invention, or a part thereof, may be distributed by transferring a program via the network.

What is claimed is:

1. A method of processing an auscultation signal, said auscultation signal being divided into a plurality of signal segments each having an individual duration of time and extending between a zero crossing in a positive or negative direction and a next zero crossing in the same positive or negative direction, said signal segments being processed into an output signal of successive signal segments, said signal segments being processed such that at least one of the signal segments is repeated at least once in said output signal, the method comprising:
analyzing the duration time of each signal segment and subjecting those signal segments that exceed a limit of 50 ms to a processing that increases the number of zero crossings during its individual duration of time so as to convert those signal segments that exceed said limit into a greater number of signal segments of a shorter duration, such that echo perception from the auscultation signal is reduced.

2. The method of processing an auscultation signal according to claim 1, further comprising:
iteratively performing said processing until the duration of time of substantially all of the signal segments of the auscultation signal is less than the limit of 50 ms.

3. The method of processing an auscultation signal according to claim 2, further comprising:
terminating the iterative processing when the auscultation signal does not comprise signal segments having a duration of time which is longer than the limit of 50 ms.

4. The method of processing an auscultation signal according to claim 3, further comprising:
terminating the iterative filtering when the auscultation signal has been filtered a specified number of times and that an indicator signal indicating termination of the filtering process is provided.

5. The method of processing an auscultation signal according to claim 2, the duration being less than 40 ms.

6. The method of processing an auscultation signal according to claim 1,
wherein said processing comprises iteratively pre-filtering the auscultation signal with a high-pass filter until the duration of time of substantially all of said signal segments is less than the limit of 50 ms.

7. The method of processing an auscultation signal according to claim 6, further comprising:
iteratively post-filtering the output signal with a filter having a transfer function corresponding to an inverse amplitude transfer function of the high-pass filter.

8. The method of processing an auscultation signal according to claim 1, further comprising:
patching signal segments having a relatively short duration of time together to form a coherent segment comprising at least three zero-crossings, the coherent segment being repeated at least once.

9. The method of processing an auscultation signal according to claim 1, wherein gradients of neighboring signal segments of the output signal are substantially equal, the neighboring signal segments being level-compensated.

10. The method of processing an auscultation signal according to claim 1, further comprising:
one of multiplying the signal divided segments and filtering the signal divided segments using a window function to level transitions between neighboring signal segments.

11. The method of processing an auscultation signal according to claim 1, further comprising:
reversing signal segments in the output signal in time.

12. The method of processing an auscultation signal according to claim 1, further comprising:
mirroring signal segments in the output signal about a time axis.

13. The method of processing an auscultation signal according to claim 1, further comprising:
pre-filtering the auscultation signal using a high-pass filter to obtain further zero crossings.

14. An a apparatus for processing an auscultation signal, the apparatus comprising:
a signal processing unit that divides the auscultation signal into a plurality of signal segments, each segment having an individual duration of time and extending between a zero crossing in a positive or negative direction and a next zero crossing in the same positive or negative direction, said signal segments being processed into an output signal of successive signal segments such that at least one signal segment is repeated at least once in said output signal,
the signal processing unit analyzing the duration time of each signal segment and subjecting those signal segments that exceed a limit of 50 ms to a processing that increases the number of zero crossings during its individual duration of time so as to convert those signal segments that exceed said limit into a greater number of signal segments of a shorter duration, such that echo perception from the auscultation signal is reduced.

15. The apparatus according to claim 14 wherein the signal processing unit is adapted to perform said processing until the duration of time of substantially all of the signal segments is less than the limit of 50 ms.

16. The apparatus according to claim 15, wherein the signal processing unit is adapted to interrupt said processing none of said signal segments have a duration of time which is longer than the limit of 50 ms.

17. The apparatus according to claim 15, the duration being less than 40 ms.

18. The apparatus according to claim 14, further comprising:
a high-pass filter that iteratively pre-filters the auscultation signal until the duration of time of substantially all of said signal segments is less than the limit of 50 ms.

19. The apparatus according to claim 18, further comprising:
a post-filter having an amplitude transfer function corresponding to an inverse amplitude transfer function of the high-pass filter that post-filters the auscultation signal.

20. The apparatus according to claim 18, wherein the iterative pre-filtering by said high-pass filter is interrupted when the auscultation signal has been filtered a specified number of times and wherein an indicator signal indicating termination of the iterative pre-filtering is provided.

21. The apparatus according to claim 14, the signal processing unit dividing the auscultation signal into signal segments such that gradients of neighboring signal segments of the output signal are substantially equal, and such that the neighboring signal segments are level-compensated.

22. An apparatus according to claim 14, the signal processing unit performs one of multiplying the signal divided segments and filtering the signal divided segments using a window function to level transitions between neighboring signal segments.

23. The apparatus according to claim 14, the signal processing unit reversing the signal segments in the output signal in time.

24. The apparatus according to claim 14, the signal processing unit mirroring the signal segments in the output signal about a time axis.

25. The apparatus according to claim 14, further comprising:
   a high-pass filter that pre-filters the auscultation signal to obtain said greater number of signal segments of shorter duration.

26. An electronic stethoscope comprising:
   at least one input transducer;
   at least one output transducer; and
   a signal processing unit divides an input signal in time into a plurality of signal segments, each segment having an individual duration of time, said signal segments being processed into an output signal of successive signal segments such that at least one signal segment is repeated at least once in said output signal, the signal processing unit processing the auscultation signal to analyze the duration of time of each signal segment and subjecting those signal segments that exceed a limit of 50 ms to a processing that increases the number of zero crossings during its individual duration of time so as to convert those signal segments that exceed said limit into a greater number of signal segments of a shorter duration, such that echo perception from the auscultation signal is reduced, said at least one output transducer reproducing said output signal.

* * * * *